United States Patent
Kido et al.

(10) Patent No.: US 10,423,758 B2
(45) Date of Patent: Sep. 24, 2019

(54) COMPUTER SYSTEM AND INFORMATION PROCESSING METHOD

(71) Applicant: Hitachi, Ltd., Chiyoda-ku, Tokyo (JP)

(72) Inventors: Kunihiko Kido, Tokyo (JP); Hiroko Otaki, Tokyo (JP)

(73) Assignee: Hitachi, Ltd., Tokyo (JP)

(*) Notice: Subject to any disclaimer, the term of this patent is extended or adjusted under 35 U.S.C. 154(b) by 314 days.

(21) Appl. No.: 15/510,375

(22) PCT Filed: Mar. 27, 2015

(86) PCT No.: PCT/JP2015/059703
§ 371 (c)(1),
(2) Date: Mar. 10, 2017

(87) PCT Pub. No.: WO2016/157314
PCT Pub. Date: Oct. 6, 2016

(65) Prior Publication Data
US 2017/0286604 A1    Oct. 5, 2017

(51) Int. Cl.
*G06F 19/00* (2018.01)
*G06Q 50/22* (2018.01)
*G16H 15/00* (2018.01)

(52) U.S. Cl.
CPC .......... *G06F 19/325* (2013.01); *G06Q 50/22* (2013.01); *G16H 15/00* (2018.01)

(58) Field of Classification Search
CPC ....... G06F 19/325; G16H 15/00; G06Q 50/22
(Continued)

(56) References Cited

U.S. PATENT DOCUMENTS

2013/0103417 A1*  4/2013  Seto ............... G06Q 50/22
                                                    705/2
2013/0218596 A1*  8/2013  Gome ............. G06Q 10/06
                                                    705/3
(Continued)

FOREIGN PATENT DOCUMENTS

JP    2004-265135 A    9/2004
JP    2006-40246 A     2/2006
(Continued)

OTHER PUBLICATIONS

Extended European Search Report issued in counterpart European Application No. 15887467.7 dated Oct. 9, 2018 (10 pages).
(Continued)

*Primary Examiner* — Bo Fan
(74) *Attorney, Agent, or Firm* — Crowell & Moring LLP

(57) ABSTRACT

A processor is configured to: acquire clinical information containing cases each indicating a disease of a patient and a medical care event performed on the patient; acquire literature information containing literature indicating a name of the disease and a word indicating the medical care event; calculate a frequency of one case indicating a combination of a plurality of diseases based on the clinical information; analyze the literature information using each of the name of the disease and the word indicating the medical care event; acquire a criterion for determining a disease for which the medical care event has been performed; acquire first relevance information indicating whether the medical care event has been performed for the disease based on the analysis result, the calculated frequency and the acquired criterion; and generate medical information indicating a relationship between the medical care event and the disease based on the first relevance information.

13 Claims, 8 Drawing Sheets

(58) Field of Classification Search
USPC .......................... 705/2, 3, 737; 702/84, 179
See application file for complete search history.

(56) References Cited

U.S. PATENT DOCUMENTS

| | | | | |
|---|---|---|---|---|
| 2013/0268290 A1* | 10/2013 | Jackson | ................ | G16B 50/00 |
| | | | | 705/2 |
| 2014/0244278 A1* | 8/2014 | Park | ....................... | G16H 50/30 |
| | | | | 705/2 |
| 2014/0278558 A1* | 9/2014 | Utsunomiya | ......... | G06F 19/324 |
| | | | | 705/3 |
| 2014/0344274 A1* | 11/2014 | Kido | .................... | G06F 16/285 |
| | | | | 707/737 |

FOREIGN PATENT DOCUMENTS

| | | |
|---|---|---|
| JP | 2008-83928 A | 4/2008 |
| JP | 2013-239158 A | 11/2013 |
| JP | 2014-120094 A | 6/2014 |
| JP | 2014-228907 A | 12/2014 |

OTHER PUBLICATIONS

International Search Report (PCT/ISA/210) issued in PCT Application No. PCT/JP2015/059703 dated Jun. 23, 2015 with English translation (5 pages).
Japanese-language Written Opinion (PCT/ISA/237) issued in PCT Application No. PCT/JP2015/059703 dated Jun. 23, 2015 (4 pages).

\* cited by examiner

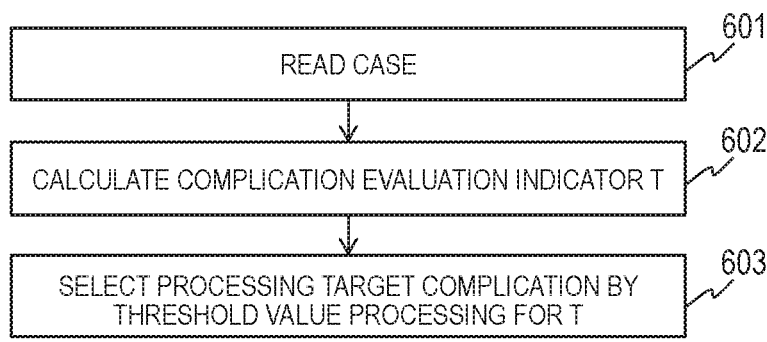
FIG. 8
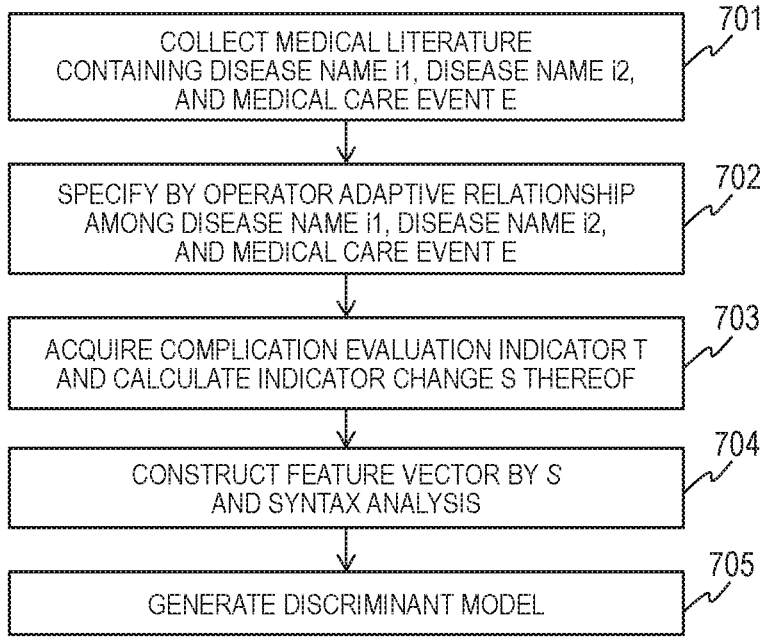
FIG. 9
FIG. 10

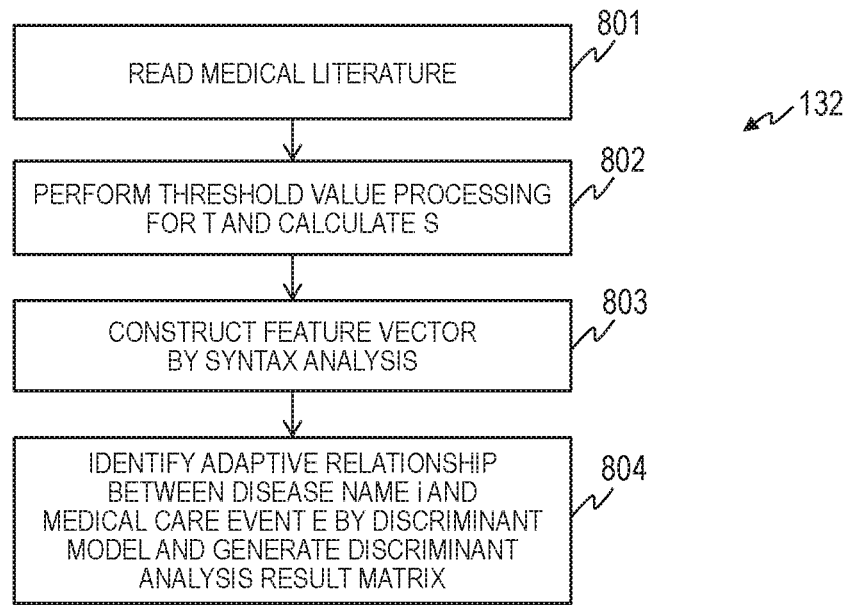
FIG. 11
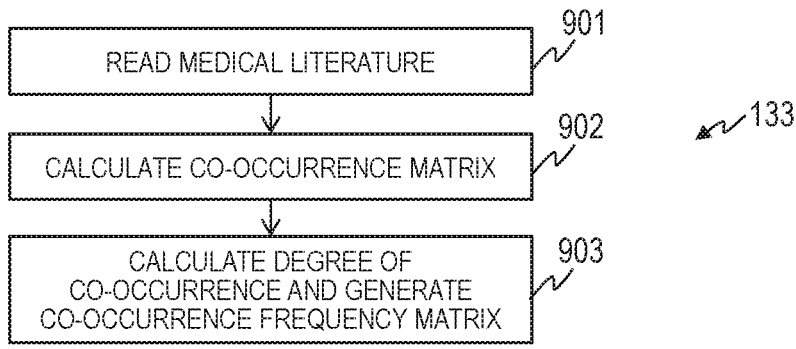
FIG. 12
FIG. 13

|  | DISEASE NAME 1 | DISEASE NAME 2 | DISEASE NAME 3 |
|---|---|---|---|
| MEDICAL CARE EVENT 1 | 100 | 10 | 13 |
| MEDICAL CARE EVENT 2 | 0 | 1 | 90 |
| MEDICAL CARE EVENT 3 | 1 | 10 | 1 |

*FIG. 14*

CO-OCCURRENCE FREQUENCY MATRIX

|  | DISEASE NAME 1 | DISEASE NAME 2 | DISEASE NAME 3 |
|---|---|---|---|
| MEDICAL CARE EVENT 1 | 0.8 | 0.1 | 0.1 |
| MEDICAL CARE EVENT 2 | 0 | 0.01 | 0.9 |
| MEDICAL CARE EVENT 3 | 0.08 | 0.8 | 0.08 |

*FIG. 15*

DISEASE NAME-MEDICAL CARE EVENT RELEVANCE TABLE

|  | DISEASE NAME 1 | DISEASE NAME 2 | DISEASE NAME 3 |
|---|---|---|---|
| MEDICAL CARE EVENT 1 | 2.7 | 0.2 | 0.1 |
| MEDICAL CARE EVENT 2 | 0 | 0.01 | 2.8 |
| MEDICAL CARE EVENT 3 | 0.08 | 2.7 | 0.18 |

*FIG. 16*

COMPUTER SYSTEM AND INFORMATION PROCESSING METHOD

BACKGROUND

This invention relates to a computer system and an information processing method.

Hitherto, there has been proposed processing of creating a cluster of disease names by representing a combination of disease names in a case using vectors with components 1 and 0 and taking a similarity degree that is based on an inner product of those vectors into consideration. This similarity degree represents a combination of disease names that are likely to occur concurrently.

Meanwhile, there is also proposed processing of identifying an adaptive relationship between a disease name and a medicine through search of the disease name and the medicine name for an attached document (for example, Patent Literature 1).

Patent Literature 1: JP 2006-040246 A

SUMMARY

Information on a relationship between a medical care event, for example, prescription, and a disease name is indispensable to, for example, processing of calculating a related cost for each disease name. It is necessary to statistically extract a relational table between the disease name and the medical care event from a clinical information database. However, a complication is mixed in a case, and thus it is difficult to isolate a relationship between the complication and the medical care event. In particular, for example, regarding a chronic disease that is likely to occur concurrently with a main disease, natures of co-occurrence of a medical care event of interest with the main disease and co-occurrence of the medical care event of interest with the chronic disease are similar to each other. Therefore, it is difficult to discriminate a relationship between the main disease and the medical care event from a relationship between the chronic disease and the medical care event.

To solve the problem, this invention is a computer system, including; a processor; and a memory, wherein the processor is configured to: acquire clinical information containing a plurality of cases, each of the plurality of cases indicating a disease of a patient and a medical care event performed on the patient; acquire literature information containing literature for indicating a name of the disease and a word indicating the medical care event; calculate a frequency of one case indicating a combination of a plurality of diseases based on the clinical information, to store the calculated frequency into the memory; analyze the literature information using each of the name of the disease and the word indicating the medical care event, to store an analysis result into the memory; acquire a criterion for determining a disease for which the medical care event has been performed; acquire first relevance information for indicating whether the medical care event has been performed for the disease based on the analysis result, the calculated frequency, and the acquired criterion, to store the first relevance information into the memory; and generate medical information for indicating a relationship between the medical care event and the disease based on the first relevance information.

According to this invention, it is possible to extract the relationship between the disease name and the medical care event accurately even for clinical information in which complications are mixed. Problems, configurations, and effects other than those described above are clarified by the following detailed description of embodiments.

BRIEF DESCRIPTION OF THE FIGURES

FIG. 8 is an explanatory diagram for illustrating the information gain matrix of this embodiment.

FIG. 9 is a flowchart for illustrating processing of the complication selection module of this embodiment.

FIG. 10 is a flowchart for illustrating processing of the model construction module of this embodiment.

FIG. 11 is a flowchart for illustrating processing of the discriminant analysis module of this embodiment.

FIG. 12 is an explanatory diagram for illustrating a determinant analysis result matrix according to this embodiment FIG. 13 is a flowchart for illustrating processing of the co-occurrence analysis module of this embodiment.

FIG. 14 is an explanatory diagram for illustrating a co-occurrence matrix of this embodiment.

FIG. 15 is an explanatory diagram for illustrating the co-occurrence frequency matrix of this embodiment.

FIG. 16 is an explanatory diagram for illustrating a disease name-medical care event relevance table of this embodiment.

DETAILED DESCRIPTION OF THE EMBODIMENTS

In the following, a description is given of an embodiment of the present invention, which relates to a system for processing medical knowledge, and more particularly, to processing for generating medical knowledge from clinical information and medical literature, with reference to the drawings.

Figure 1:
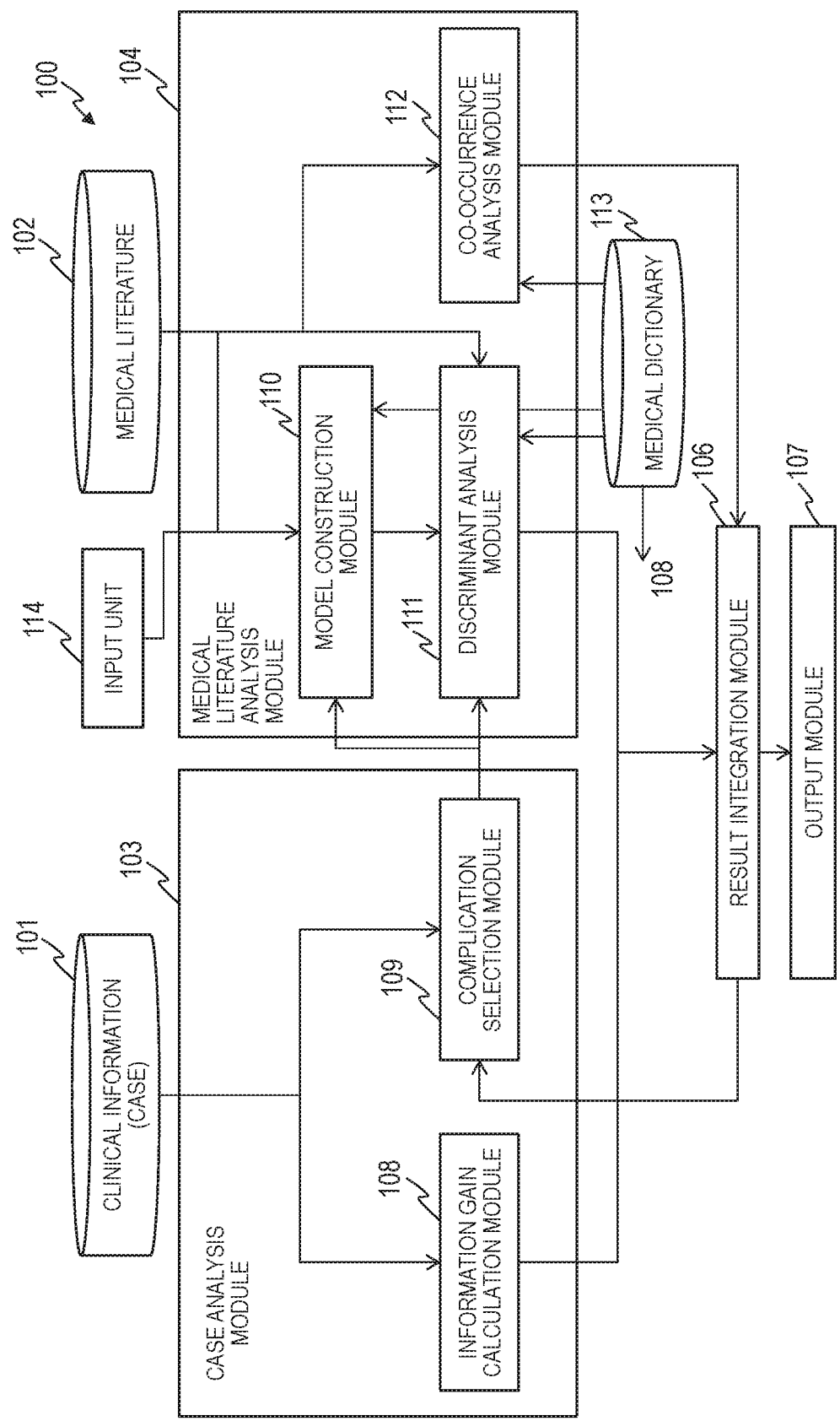
FIG. 1 is a block diagram for illustrating functions of a computer system according to this embodiment.

FIG. 1 is a block diagram for illustrating functions of a computer system 100 according to this embodiment.

The computer system 100 according to this embodiment includes a clinical information DB 101, a medical literature DB 102, a medical dictionary 113, an input unit 114, a case analysis module 103, a medical literature analysis module 104, a result integration module 106, and an output module 107. In this embodiment, a person who receives a medical checkup, a medical treatment, for example, surgery, or a prescription of a medicine at a facility is referred to as a patient. The patient in this embodiment includes a human and an animal.

Further, a medical care event in this embodiment is a word indicating medical matters other than a disease name, and includes, for example, a medical treatment, a prescribed medicine, and medical appliances (a catheter and a gastro-camera) to be used. Further, a disease in this embodiment indicates an unhealthy condition of a patient's body or a patient's mind, and includes, for example, a myocardial infarction, diabetes, a stomach cancer, depression, and a bone fracture.

Further, a medical care in this embodiment indicates all the medical treatments such as a diagnosis, a cure, and a prescription. Further, a facility in this embodiment includes, in addition to a hospital and a clinic, all the places where a medical worker may perform a medical treatment on a patient, such as a house, a welfare facility, and an ambulance.

The clinical information DB 101 includes a case indicating, for example, a history of a patient receiving medical treatments at a facility and the name of a disease caught by the patient. The clinical information DB 101 is updated by, for example, an operator or an administrator (hereinafter referred to as an operator) of the computer system 100 according to this embodiment.

The medical literature DB 102 includes content of medical literature, and includes, for example, content of a medical book and a paper in which a treatment method is described. The medical dictionary 113 indicates medical terminology. The medical literature DB 102 and the medical dictionary 113 are updated by, for example, an operator in advance.

The case analysis module 103 is a function module configured to acquire an adaptive relationship between a disease name and a medical care event based on the clinical information DB 101. The adaptive relationship in this embodiment indicates a degree of a medical care event received by a patient when the patient has caught a disease indicated by a disease name, and indicates whether or not the medical care event is performed to tackle the disease.

The medical literature analysis module 104 is a function module configured to acquire the adaptive relationship between a disease name and a medical care event based on the medical literature DB 102 or based on the medical literature DB 102 and the clinical information DB 101.

The result integration module 106 is a function module configured to integrate a processing result of the case analysis module 103 and a processing result of the medical literature analysis module 104. The output module 107 is a function module configured to output to the operator or user of the computer system 100 according to this embodiment medical knowledge indicating a relationship between a disease name and a medical care event based on a processing result of the result integration module 106.

The input unit 114 is a function module configured to receive a criterion for determining the adaptive relationship between a medical care event and a disease name from an operator or the like.

The case analysis module 103 includes an information gain calculation module 108 and a complication selection module 109. The information gain calculation module 108 is a function module configured to acquire a frequency of a medical care event received by a patient that has caught a disease indicated by a disease name based on the clinical information DB 101, and to acquire a relationship between the disease name and the medical care event based on the frequency.

The complication selection module 109 is a function module configured to calculate an indicator (complication evaluation indicator) indicating whether or not a plurality of diseases are complications based on the clinical information DB 101.

The medical literature analysis module 104 includes a model construction module 110, a discriminant analysis module 111, and a co-occurrence analysis module 112. The model construction module 110 is a function module configured to generate a determination model for determining whether or not a disease name and a medical care event are related to each other based on the medical literature DB 102 and an input value from the input unit 114.

The discriminant analysis module 111 is configured to acquire the adaptive relationship between a disease name and a medical care event based on the determination model, the complication evaluation indicator, and the medical literature DB 102. The co-occurrence analysis module 112 is configured to acquire the adaptive relationship between a disease name and a medical care event based on the medical literature DB 102.

Figure 2:
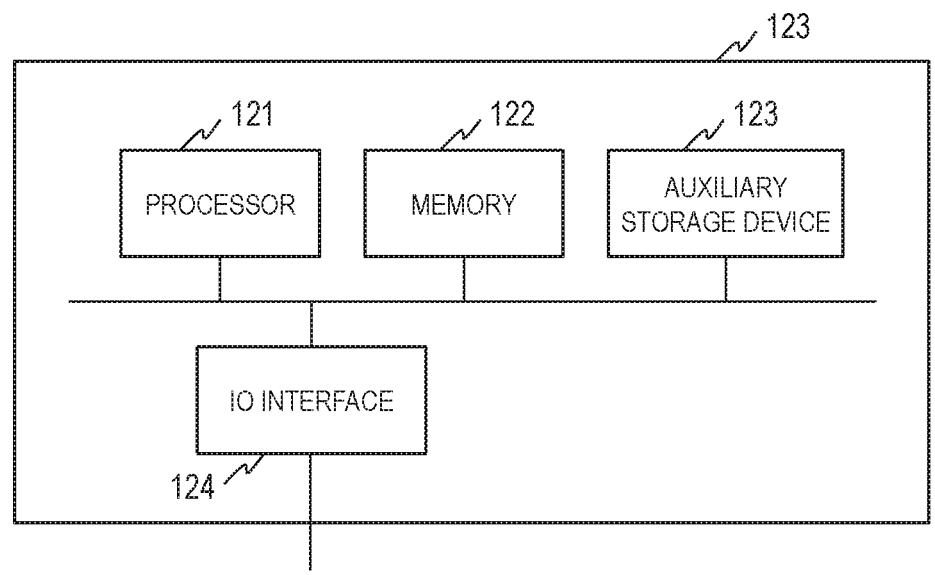
FIG. 2 is a block diagram for illustrating a physical configuration of the computer system according to this embodiment.

FIG. 2 is a block diagram for illustrating a physical configuration of the computer system 100 according to this embodiment.

The computer system 100 according to this embodiment is formed of at least one computer. The computer system 100 includes a processor 121, a memory 122, an auxiliary storage device 123, and an IO interface 124.

The computer system 100 implements functions of the case analysis module 103, the medical literature analysis module 104, the result integration module 106, and the output module 107 illustrated in FIG. 1 by the processor executing programs stored in the memory 122. For example, the function of the information gain calculation module 108 is implemented through processing by an information gain calculation program, and the function of the discriminant analysis module 111 is implemented through processing by a discrimination analysis program.

The memory 122 includes a ROM, which is a nonvolatile storage element, and a RAM, which is a volatile storage element. The ROM stores data, for example, a fixed program (for example, BIOS). The RAM is a high-speed and volatile storage element, for example, a dynamic random access memory (DRAM), and temporarily stores a program stored in the auxiliary storage device 123 and data to be used at the time of execution of the program.

The auxiliary storage device 123 is, for example, a large-capacity and nonvolatile storage device such as a magnetic storage device (HDD) or a flash memory (SSD). Further, the auxiliary storage device 123 stores a program to be executed by the processor 121 and data (for example, complication evaluation indicator described later) to be used at the time of execution of the program.

Programs for implementing the function modules of this embodiment are read from the auxiliary storage device 123, loaded into the memory 122, and executed by the processor 121. The auxiliary storage device 123 stores the clinical information DB 101, the medical literature DB 102, and the medical dictionary 113 as data, and further stores the processing results produced by respective function modules.

Programs to be executed by the processor 121 are provided to the computer system 100 via a removable medium (for example, a CD-ROM or a flash memory) or a network, and are stored in the auxiliary storage device 123. Thus, the computer system 100 may include an interface for reading data from the removable medium.

The IO interface 124 is an interface for coupling to an input device and an output device. In this context, the input device is a keyboard or a mouse, and the output device is a display or a printer. Further, the input device and the output device may be one device, for example, a tablet terminal.

The operator of the computer system 100 according to this embodiment inputs the program and data of the computer system 100 via the input device. Further, the operator or the user acquires generated medical information (medical knowledge in this embodiment) via the output device.

The computer system 100 is a computer system formed on physically one computer or on a logically or physically plurality of computers, and the above-mentioned programs may operate as separate threads on the same computer, or operate on a virtual computer constructed on a plurality of physical computer resources.

Figure 3:
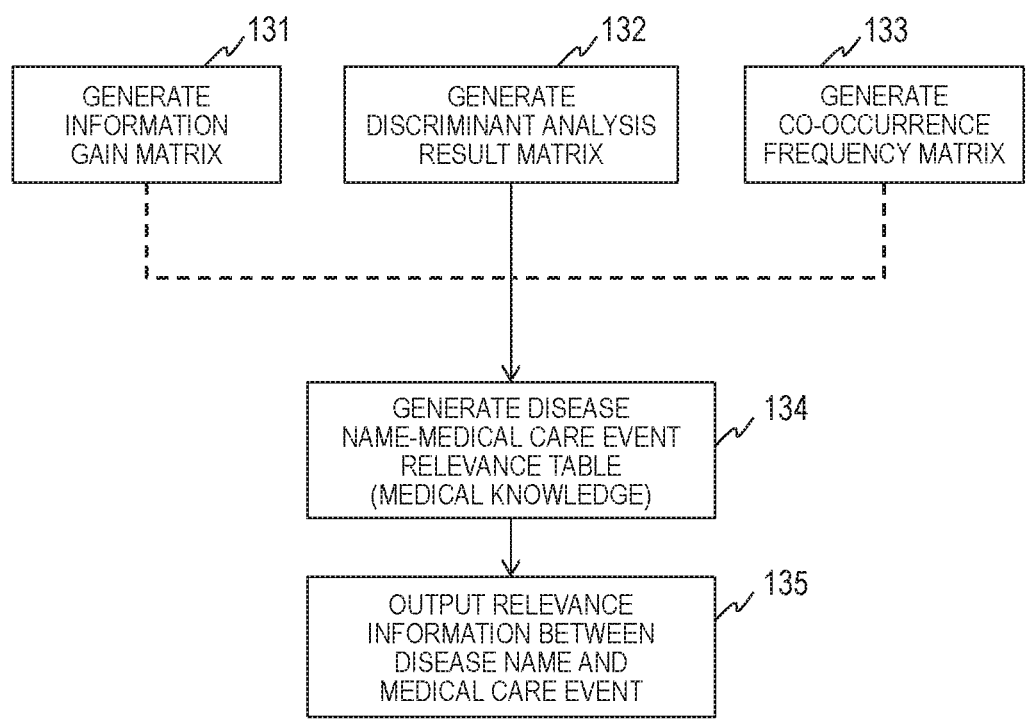
FIG. 3 is a flowchart for illustrating an outline of processing of the computer system according to this embodiment.

FIG. 3 is a flowchart for illustrating an outline of processing of the computer system 100 according to this embodiment.

The computer system 100 according to this embodiment generates with three methods pieces of information indicating the relationship between a disease name and a medical care event, and generates medical knowledge using those pieces of information. Specifically, the information gain calculation module 108 generates an information gain matrix (131), the discriminant analysis module 111 generates a determinant analysis result matrix (132), and the co-occurrence analysis module 112 generates a co-occurrence frequency matrix (133).

Then, the result integration module 106 generates a disease name-medical care event relevance table using the information gain matrix, the determinant analysis result matrix, and the co-occurrence frequency matrix (134). The disease name-medical care event relevance table is medical knowledge indicating a relationship between a disease and a medical care event.

Then, the output module 107 outputs to the operator or medical personnel the information generated based on the disease name-medical care event relevance table (135).

The result integration module 106 according to this embodiment may generate a disease name-medical care event relevance table using at least one of the information gain matrix, the determinant analysis result matrix, and the co-occurrence frequency matrix. In particular, the result integration module 106 of this embodiment can generate the disease name-medical care event relevance table using only the determinant analysis result matrix, which means that the result integration module 106 can generate the disease name-medical care event relevance table using both of the clinical information DB 101 and the medical literature DB 102.

Further, the result integration module 106 of this embodiment can generate accurate information indicating the relationship between a disease name and a medical care event by using the information gain matrix and the co-occurrence frequency matrix in addition to the determinant analysis result matrix in order to generate the disease name-medical care event relevance table.

Figures 4, 5:
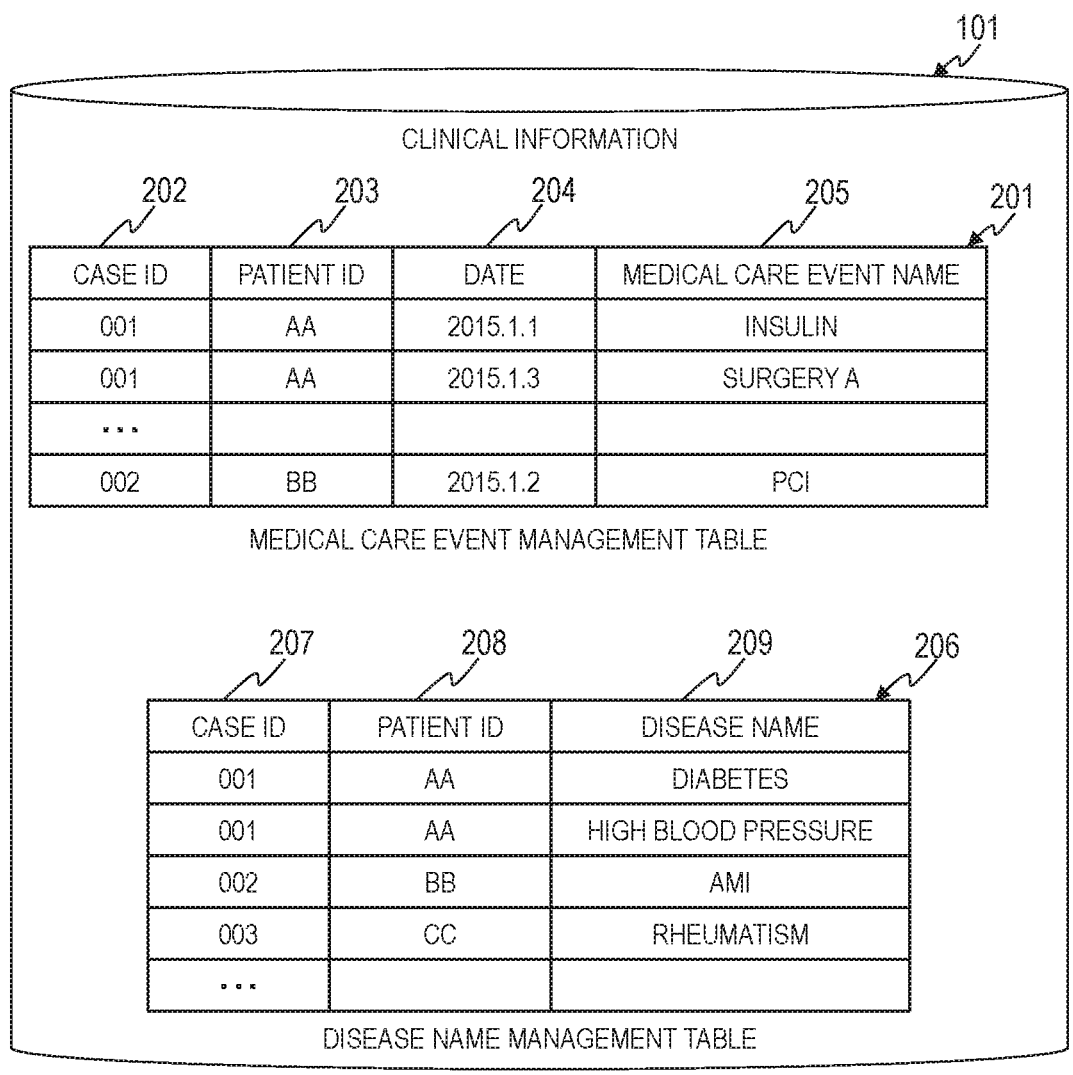
FIG. 4 is an explanatory diagram for illustrating the clinical information DB of this embodiment.
FIG. 5 is a table for showing the medical dictionary of this embodiment.

FIG. 4 is an explanatory diagram for illustrating the clinical information DB 101 of this embodiment.

The clinical information DB 101 includes a medical care event management table 201 and a disease name management table 206. The medical care event management table 201 indicates the history of a patient receiving a medical care event at a facility. The disease name management table 206 indicates the name of a disease of a patient.

The medical care event management table 201 includes a case ID 202, a patient ID 203, a date 204, and a medical care event name 205.

The case ID 202 is an ID assigned to a case. The case ID 202 is arbitrarily assigned by the operator of this embodiment. The case in this embodiment is a history of a series of medical care events that a patient has received at a facility, and indicates, for example, a history of medical care events in hospitalization, a history of medical care events at hospital visits, and a history of first aid measures.

One case ID is assigned to a series of medical care events. For example, when a patient is hospitalized for a predetermined period at a hospital, the operator assigns a unique case ID to hospitalization in the predetermined period. Further, for example, when a patient does not stay but goes to hospital every day for a predetermined period, the operator assigns a unique case ID to the hospital visits in the predetermined period.

The patient ID 203 is an ID assigned to a patient who receives a medical care event.

The date 204 indicates the date on which a medical care event indicated by the medical care event name 205 started. Further, when the medical care event name 205 indicates a medical care event completed in one day, the date 204 indicates the date on which the medical care event was performed. For example, when administration of a medicine started on the second day of the hospitalization period, the date 204 indicates the day of the second clay of the hospitalization period.

The medical care event name 205 indicates a medical care event performed on a patient, and when two or more medical care events are started on the same day, a record may be generated for each medical care event. The medical care event name 205 is, for example, an injection, an examination, surgery, a prescription, and a treatment.

The disease name management table 206 includes a case ID 207, a patient ID 208, and a disease name 209. The case ID 207 is an ID assigned to a case. The case ID 207 corresponds to the case ID 202. The patient ID 208 is an ID assigned to a patient. The patient ID 208 corresponds to the patient ID 203.

The disease name 209 is the name of a disease that is the cause of a medical care given to a patient in a case indicated by the case ID 207. The disease in this embodiment is a disease handled by medical departments in all medical fields such as internal medicine, surgery, and ophthalmology.

FIG. 5 is a table for showing the medical dictionary 113 of this embodiment.

The medical dictionary 113 of this embodiment classifies the disease name and words other than the disease name. The medical dictionary 113 contains a classification 301 and a name 302.

The classification 301 indicates the classification of the name 302, namely, the disease name and classification names other than the disease name. The classification names other than the disease name includes, for example, a prescription name, an injection name, an examination name, a surgery name, and a treatment name. The name 302 indicates a name used in the medical field.

The information gain calculation module 108, the model construction module 110, the discriminant analysis module 111, and the co-occurrence analysis module 112 refer to the medical dictionary 113 to acquire a disease name, and in addition, acquire a word indicating a medical care event from the name indicating medical matters other than the disease name. In this manner, the computer system 100 according to this embodiment can define the disease name and names corresponding to medical care events in accordance with the medical dictionary 113.

Figure 6:
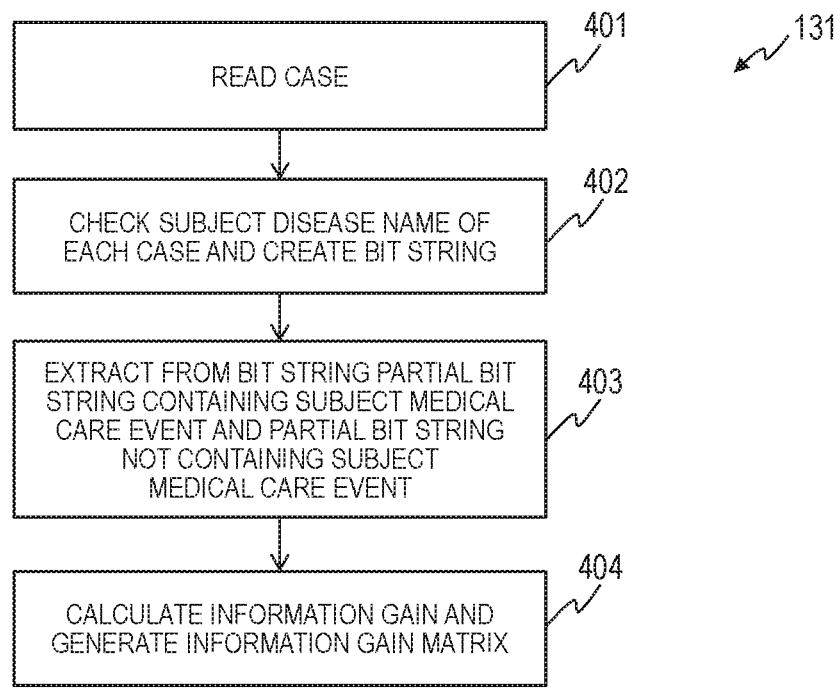
FIG. 6 is a flowchart for illustrating processing to be executed by the information gain calculation module of this embodiment.

FIG. 6 is a flowchart for illustrating processing to be executed by the information gain calculation module 108 of this embodiment.

The information gain calculation module 108 reads case data from the clinical information DB 101 (401). In this context, the case data means all the records of the medical care event management table 201 and all the records of the disease name management table 206. In Step 401, the information gain calculation module 108 reads the case data into the memory 122.

Next, the information gain calculation module 108 generates a bit string indicating whether or not, in the read disease name management table 206, each of cases indicated in the clinical information DB 101 contains a subject disease name i (402).

In this context, the subject disease name i means one disease name selected from among disease names indicated by the names 302 within all the records whose classifications 301 of the medical dictionary 113 are the disease name. In Step 402, the information gain calculation module 108 selects all the disease nannies from the medical dictionary 113, and generates a bit string for each selected disease name.

Specifically, in Step 402, the information gain calculation module 108 of this embodiment associates one bit with one case ID 207. When the disease names 209 of one or more records indicating one case ID 207 contain the subject disease name i, the information gain calculation module 108 stores 1 to a bit corresponding to the case ID 207. On the contrary, when the subject disease name i is not contained, the information gain calculation module 108 stores 0 to a bit corresponding to the case ID 207.

Figure 7:
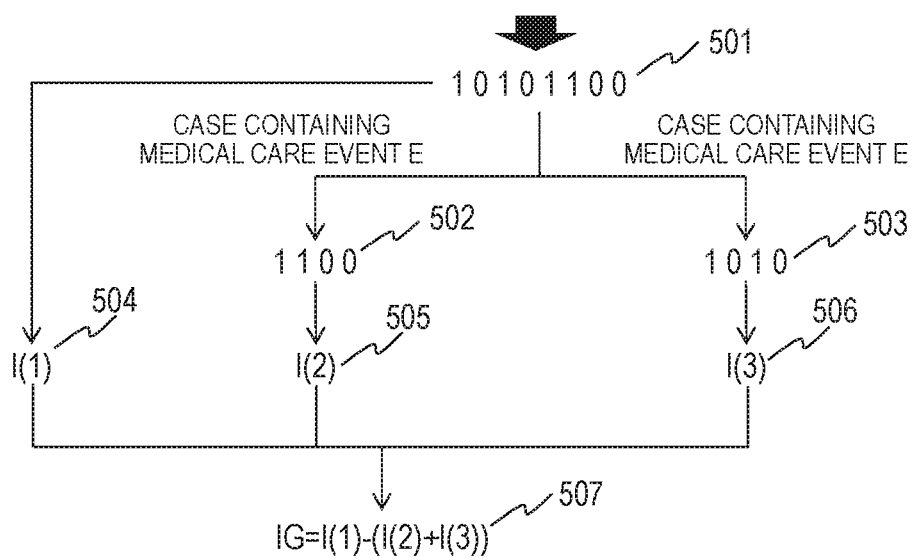
FIG. 7 is an explanatory diagram for illustrating a result of processing by the information gain calculation module of this embodiment

FIG. 7 is an explanatory diagram for illustrating a result of processing by the information gain calculation module 108 of this embodiment.

As a result of Step 402, the information gain calculation module 108 generates a bit string 501 illustrated in FIG. 7.

After Step 402, the information gain calculation module 108 generates a bit string 502 indicating a case in which a subject medical care event E is performed and a bit string 503 indicating a case in which a subject medical care event E is performed by dividing the bit string 501 into those bit strings (403).

In this context, the subject medical care event E is one word selected from among the names 302 whose corresponding classifications 301 of the medical dictionary 113 are not disease names. The information gain calculation module 108 generates the bit string 502 and the bit string 503 for each subject medical care event E among medical care events, which are words other than the disease name.

In Step 403, specifically, the information gain calculation module 108 identifies a record of the medical care event management table 201 whose case ID 202 is the same as the case ID 207. Then, the information gain calculation module 108 extracts a bit corresponding to the case ID 207 for which the subject medical care event E is contained in the medical care event name 205 of the identified record, and generates the bit staring 502 containing only the extracted bit.

Further, the information gain calculation module 108 extracts from the bit string 501 a bit corresponding to the case ID 207 for which the subject medical care event E is not contained in the medical care event name 205 of the identified record, and generates the bit string 503 containing only the extracted bit.

After Step 403, the information gain calculation module 108 calculates an information gain matrix indicating a medical care event particularly often performed for the disease name (404). Specifically, the information gain calculation module 108 uses a probabilistic complexity to calculate an information gain 504 from the bit string 501, an information gain 505 from the bit string 502, and an information gain 506 from the bit string 503.

The information gain calculation module 108 uses Expression (1) to calculate the information gains 504, 505, and 506.

$$I(i,E,x) = \min\{m1, m-m1\} + \lambda\sqrt{(m \log m)}$$

($m$: number of bits contained in bit string, $m1$: number of times of appearance of 1, $\lambda$: weighting for right term) (1)

In Expression (1), x is an identifier of the information gain. Thus, the information gain 504 is I(i,E,1), the information gain 505 is I(i,E,2), and the information gain 506 is I(i,E,3). The information gains 504, 505, and 506 are each a two-dimensional matrix of the disease name i and the medical care event E.

The information gain 504 (I(i,E,1)) is calculated only based on the disease name without depending on the medical care event E Thus, the information gain calculation module 108 uses the value of I(i,E,1) calculated for one disease name i to reproduce I(i,E,1), which is calculated for a combination of one disease name i and all the medical care events E.

Then, the information gain calculation module 108 uses the information gains 504, 505, 506, and Expression (2) to generate an information gain matrix IG(i,E). The information gain matrix 507 illustrated in FIG. 7 indicates an information gain matrix that is based on Expression (2).

$$IG(i,E) = I(i,E,1) - (I(i,E,2) + I(i,E,3))$$ (2)

The information gain matrix IG(i,E) is a matrix for representing whether or not the medical care event E is specific to the disease name (whether or not the medical care event E is performed particularly often for the disease name i).

As the calculated value of the information gain matrix IG(i,E) becomes larger, the combination of the disease name i and the medical care event E is specific and an appropriate relationship, and the medical care treatment of the medical care event E is often adopted for the disease of the disease name i. As the calculated value of the information gain matrix IG(i,E) becomes smaller, the medical care treatment of the medical care event E is rarely adopted for the disease of the disease name i, or the medical care treatment of the medical care event E is adopted for a large number of diseases and is not adopted for the disease name i particularly in many cases.

For example, an infusion solution is a medicine that is often used in any disease. Thus, when the medical care event E is an infusion solution, the value of the information gain 505 calculated for the infusion solution becomes particularly large. Specifically, the right term ($\lambda\sqrt{(m \log m)}$) and the value of the information gain I(i,(infusion solution),2) are large, and the value of the information gain matrix IG(i,(infusion solution)) is small. Thus, when the value of the information gain matrix IG(i,(infusion solution)) is small, the combination of the disease name i and the infusion solution is not specific.

The information gain calculation module 108 stores the calculated information gain matrix IG(i,E) into the memory 122 or the auxiliary storage device 123. The information gain calculation module 108 can use the matrix indicating a relevance of the disease name i to the medical care event E, which is based only on the clinical information DB 101, for generation of the disease name-medical care event relevance table by generating the information gain matrix IG(i,E).

FIG. 8 is an explanatory diagram for illustrating the information gain matrix IG(i,E) of this embodiment.

An information gain matrix 1101 of FIG. 8 is an example of the information gain matrix IG(i,E), and a column 1102 indicates a disease name and a row 1103 indicates a medical care event.

FIG. 9 is a flowchart for illustrating processing of the complication selection module 109 of this embodiment.

The complication selection module 109 reads case data from the clinical information DB 101 into the memory 122 similarly to Step 401 (601).

After Step 601, the complication selection module 109 calculates a complication evaluation indicator T, which is an indicator for determining whether or not a disease name i1 and a disease name i2 are complications after the number of days k has passed since a date t0 based on Expression (3) and the case data (602). In this manner, the complication selection module 109 can calculate an indicator for determining whether or not the disease name i1 and the disease name i2 are complications.

In this context, the elapsed period k is any one of the number of days a0 and the number of days a1. Further, the date t0 is the earliest day among days indicated by the date 204 of the medical care event management table 201 in this embodiment, but may be specified by the operator. Further, the number of days a1 is larger than the number of days a0. The number of days a0 and the number of days a1 are input by the operator in advance.

$T(i1,i2,k)$=(number of cases containing both of disease name $i1$ and disease name $i2$ in period until number of days $k$ has passed since date $t0$)/Max(number of cases containing at least disease name $i1$ in period until number of days $k$ has passed since date $t0$, number of cases containing at least disease name $i2$ in period until number of days $k$ has passed since date $t0$) (3)

As the calculated complication evaluation indicator T(i1,i2,k) becomes closer to 1, the complication evaluation indicator T(i1,i2,k) more strongly indicates that both of the disease name i1 and the disease name i2 appear in one case. Thus, the complication evaluation indicator T indicates the frequency of both of the disease name i1 and the disease name i2 being contained in one case.

In this context, the disease name i1 and the disease name i2 are the names 302 of all the identified records whose classifications 301 of the medical dictionary 113 are the disease name. Further, the complication selection module 109 may calculate the complication evaluation indicator T for three or more disease names. In this case, the complication selection module 109 calculates the complication evaluation indicator T by dividing the number of cases containing a plurality of disease names by the maximum value of the number of cases containing at least one disease name.

In Step 602, the complication selection module 109 identifies in the medical care event management table 201 a record contained in a period until the number of days k has passed since the date t0, and identifies in the disease name management table 206 a record whose case ID 207 is the same as the case ID 202 of the identified record. Then, the complication selection module 109 uses the identified record of the disease name management table 206 to acquire the number of cases containing both of the disease name i1 and the disease name i2, the number of cases containing at least the disease name i1, and the number of cases containing at least the disease name i2.

The complication selection module 109 calculates the complication evaluation indicator T(i1,i2,a0) of when the number of days k is a0, and the complication evaluation indicator T(i1,i2,a1) of when the number of days k is a1. The complication selection module 109 stores the calculated complication evaluation indicator T into the memory 122 or the auxiliary storage device 123.

After Step 602, the complication selection module 109 compares the calculated complication evaluation indicator T(i1,i2,k) with a predetermined threshold value, and selects as a complication combination the combination of the disease name i1 and the disease name i2 for which the calculated complication evaluation indicator T becomes higher than the predetermined threshold value. Then, the complication selection module 109 stores the selected complication combination into the memory 122 or the auxiliary storage device 123.

FIG. 10 is a flowchart for illustrating processing of the model construction module 110 of this embodiment.

The model construction module 110 collects from the medical literature DB 102 medical literature files (files containing content of, for example, papers and books) containing all of the disease name i1, the disease name i2, and the medical care event E (701). Specifically, the model construction module 110 identifies by full-text search from text of medical literature held by the medical literature DB 102 literature files containing all the names of the disease name i1, the disease name i2, and the medical care event E.

In this context, the disease name i1 and the disease name i2 are disease names selected from the names 302 of records whose classifications 301 of the medical dictionary 113 are the disease name. Further, the medical care event E is a name selected from the names 302 of records whose classifications 301 of the medical dictionary 113 are other than the disease name.

After Step 701, the model construction module 110 receives via the input unit 114 a medically appropriate adaptive relationship among the disease name i1, the disease name i2, and the medical care event E, which is input by the operator (702).

When the medical care event E is performed for the disease name i1, the operator inputs via the input unit 114 information indicating the adaptive relationship such as (disease name i1, medical care event E)=1 and (disease name i2, medical care event E)=0. Further, when the medical care event E is performed for the disease name i2, the operator inputs via the input unit 114 information indicating the adaptive relationship such as (disease name i1, medical care event E)=0 and (disease name i2, medical care event E)=1.

After Step 702, the model construction module 110 acquires the complication evaluation indicator T(i1,i2,k) (k=a0,a1) calculated by the complication selection module 109, and calculates an indicator change S of the complication evaluation indicator T using Expression (4) (703).

$S(i1,i2)=|T(i1,i2,a1)-T(i1,i2,a0)|/T(i1,i2,a0)$ (4)

The indicator change S(i1,i2) is a temporal change amount of the complication evaluation indicator T. The model construction module 110 can calculate an indicator indicating the change in occurrence of the complication along with passage of time by calculating the indicator change S using Expression (4).

When the indicator change S(i1,i2) is a numerical value close to 0, that is, when the complication evaluation indicator T(i1,i2,k) does not change even when the elapsed period has increased from the number of days a0 to the number of days a1 and the number of cases has increased, either one of the disease name i1 and the disease name i2 is highly likely to be a chronic disease, for example, diabetes. For example, a patient with a heart disease is highly likely to have a chronic disease such as a high blood pressure or diabetes.

On the contrary, when the indicator change S(i1,i2) is equal to or more than a predetermined threshold value, either one of the disease name i1 and the disease name i2 is highly likely to be an acute complication that occurs during hospitalization. For example, infectious diseases that occur after surgery can be given. Infections occur at a certain rate, but do not co-occur as frequently as chronic diseases, and thus the value of the indicator change S(i1,i2) is large.

In this embodiment, the number of days a0 and the number of days a1 are given as the elapsed period k, but three or more patterns of the number of days may be given as the elapsed period k. Further, the indicator change S may be an average value of the temporal change amounts of the complication evaluation indicator T or may be a statistical value thereof, for example, a maximum value.

After Step 703, the complication selection module 109 generates a feature vector using the following methods 1 to 4 by syntax analysis for each indicator change S(i1,i2) calculated in Step 703 or for each literature file read in Step 701.

Method 1: store a base form of a verb of a sentence containing the disease name i1 into a first component (when the verb is a be-verb, store an adjective or a noun, which is a complement), store a value indicating whether the disease name i1 is a subject (=1), a predicate (=0), or another value (−1) into a second component, and store the indicator change S(i1,i2) into a third component. The feature vector acquired with Method 1 is a three-dimensional vector (base form of verb/adjective/noun, 1/0/−1, S).

Method 2: store a base form of a verb of a sentence containing the disease name i2 into a first component (when the verb is a be-verb, store an adjective or a noun, which is a complement), store a value indicating whether the disease name i2 is a subject (=1), a predicate (=0), or another value (−1) into a second component, and store the indicator change S(i1,i2) into a third component. The feature vector acquired with Method 2 is a three-dimensional vector (base form of verb/adjective/noun, 1/0/−1, S).

Method 3: store a base form of a verb of a sentence containing both of the disease name i1 and the medical care event E into a first component (when the verb is a be-verb, store an adjective or a noun, which is a complement), store a value indicating whether the disease name i1 is a subject (=1), a predicate (=0), or another value (−1) into a second component, store a value indicating whether or not the medical care event E is a subject (=1), a predicate (=0), or another value (−1) into a third component, and store the indicator change S(i1,i2) into a fourth component. The feature vector acquired with Method 3 is a four-dimensional vector (base form of verb/adjective/noun, 1/0/−1, 1/0/−1, S).

Method 4: store a base form of a verb of a sentence containing both of the disease name i2 and the medical care event E into a first component (when the verb is a be-verb, store an adjective or a noun, which is a complement), store a value indicating whether the disease name i2 is a subject (=1), a predicate (=0), or another value (−1) into a second component, store a value indicating whether or not the medical care event E is a subject (=1), a predicate (=0), or another value (−1) into a third component, and store the indicator change S(i1,i2) into a fourth component. The feature vector acquired with Method 4 is a four-dimensional vector (base form of verb/adjective/noun, 1/0/−1, 1/0/−1, S).

Now, in the following, a description is given of an example of a case in which the disease name i1 is "ST-segment elevation myocardial infarction (STEMI)", the disease name i2 is "diabetes", and the medical care event E is "percutaneous coronary intervention (PCI)". The indicator change S(i1,i2) is assumed to be 0.1 for the time being.

When the document file acquired from the medical literature DB 102 contains "ST-segment elevation myocardial infarction (STEMI) who underwent primary percutaneous coronary intervention (PCI)", the disease name i1 is a subject, "underwent" is a verb, and the medical care event E is a predicate.

Thus, the model construction module 110 uses Method 3 described above to generate the feature vector (undergo, 1, 0, 0.1) for the sentence.

Further, when the document file acquired from the medical literature DB 102 contains "patients with preinfarction AP was consistently observed across subgroups stratified by total ischemic time, initial Thrombolysis In Myocardial Infarction flow grade, hemodynamic status, infarct location, and diabetes mellitus.", the disease name i2 is neither a subject nor a predicate and "stratified" is a verb.

Thus, the model construction module 110 uses Method 2 described above to generate the feature vector (stratify, −1, 0.1) for the sentence.

Next, in the following, a description is given of an example of a case in which the disease name i1 is "stroke", the disease name i2 is "AMI", and the medical care event E is "PCI". The indicator change S(i1,i2) is assumed to be 0.6 for the time being.

When the sentence acquired from the medical literature DB 102 is "An inhospital ischemic stroke occurred", the disease name i1 is a subject, and "occurred" is a verb.

Thus, the model construction module 110 uses Method 1 described above to generate the feature vector (occur, 1, 0.6) for the sentence.

Further, when the sentence acquired from the medical literature DB 102 is "Percutaneous coronary intervention (PCI) and statins were independently associated with a reduced risk of stroke after discharge from hospital.", the disease name i1 is a subject, "associated" is a verb, and the medical care event E is a predicate.

Thus, the model construction module 110 uses Method 3 described above to generate the feature vector (associate, 1, 0, 0.6) for the sentence.

When the sentence acquired from the medical literature DB 102 is "Ischemic stroke is a more common complication after an AMI", the disease name i1 is a subject, the disease name i2 is a predicate, and a noun, which is a complement, is "complication".

Thus, the model construction module 110 uses Method 3 described above to generate the feature vector (complication, 1, −1, 0.6) for the sentence.

After Step 704, the model construction module 110 sets an objective variable in the disease name i1=medical care event E to 1 and an objective variable in the disease name i2=medical care event E to 0, to thereby perform discriminant analysis for four kinds of feature vectors and generate a discriminant model (705). Then, the model construction module 110 performs discriminant analysis for a three-dimensional vector or a four-dimensional vector constructed with an average of discriminant distances of Methods 1 to 4 to generate a total discriminant model.

In Step 705, the model construction module 110 uses an adaptive relationship between the disease name i and the medical care event E received in Step 702 ((disease name i, medical care event E)=1 or 0) and the feature vector generated in Step 704 to learn a discriminant model for discriminating whether or not the disease name i and the medical care event E are adaptive (whether or not the medical care event E is performed for the disease name i). The discriminant analysis may be performed by a support vector machine because the feature vector has a high dimension, or may be performed in any method.

Specifically, the model construction module 110 associates the adaptive relationship received in Step 702 with the feature vector generated in Step 704, to thereby divide the generated feature vector into a feature vector indicating the disease name i having an adaptive relationship with the medical care event E and a feature vector indicating the disease name i not having an adaptive relationship with the medical care event E.

Then, as a result of the division, the model construction module 110 identifies a discriminant curve, which is a border of a group of the generated feature vectors, and stores the discriminant model and the discriminant curve into the memory 122 or the auxiliary storage device 123. The discriminant analysis module 111 described later uses the identified discriminant curve to determine whether or not the generated feature vector is the one indicating a medical care event performed for the disease name i.

In Step 705, the model construction module 110 associates the adaptive relationship between the disease name i1 and the medical care event E with the feature vector generated with Method 1 or 3, and associates the adaptive relationship between the disease name i2 and the medical care event E with the feature vector generated with Method 2 or 4.

The operator may input a discriminant model without the model construction module 110 generating a discriminant model.

FIG. 11 is a flowchart for illustrating processing of the discriminant analysis module 111 of this embodiment.

The discriminant analysis module 111 reads a medical literature file from the latest medical literature DB 102 (801).

Next, the discriminant analysis module 111 acquires the latest complication evaluation indicators T(i1,i2,k) calculated in Step 602, and identifies the complication evaluation indicator T that is larger than a predetermined threshold value from the acquired complication evaluation indicators T. Then, the discriminant analysis module 111 uses the identified complication evaluation indicator T(i1,i2,k) and Expression (4) to calculate the indicator change S (802).

When the clinical information DB 101 is updated, the complication evaluation indicator T acquired in Step 802 may be different from the complication evaluation indicator T acquired by the model construction module 110 in Step 703. In Step 802, the discriminant analysis module 111 can perform discriminant analysis described later for a feature vector of the combination of the disease name i1 and the disease name i2, which are highly like to be complications, by using the complication evaluation indicator T that is larger than the predetermined threshold value.

After Step 802, the discriminant analysis module 111 generates a feature vector by syntax analysis using the same method as Step 704 for each indicator change S(i1,i2) calculated in Step 702 and for each medical literature file read in Step 801 (803).

When the medical literature DB 102 is not updated, the first component and the second component of the feature vector (when the feature vector is a four-dimensional vector, the third component) generated in Step 803 are the same as the first component and the second component of the feature vector (when the feature vector is a four-dimensional vector, the third component) generated in Step 704. However, the feature vector generated in Step 803 and the feature vector generated in Step 704 may have different values of the indicator changes S for the last component.

After Step 803, the discriminant analysis module 111 uses the discriminant curve of the discriminant model (for the disease name i1, the disease name i2, and the medical care event E) generated in Step 705 to perform discriminant analysis for the feature vector (for the disease name the disease name i2, and the medical care event E) generated in Step 802, to thereby discriminate the adaptive relationship between the disease name i1 and the medical care event E from the adaptive relationship between the disease name i2 and the medical care event E.

For example, when the feature vector generated in Step 704 and the feature vector generated in Step 802 are compared with each other to calculate a distance and the calculated distance is within a predetermined range, the discriminant analysis module 111 may associate the adaptive relationship (received in Step 702) corresponding to the feature vector generated in Step 704 with the feature vector generated in Step 802.

The discriminant analysis module 111 compares the components of the feature vector generated based on the medical literature DB 102 with the components of the discriminant model, to thereby be able to use, for example, positions and roles of a disease name in the literature file and a medical care vector as parameters for determining a relevance of the disease to the medical care vector. Then, the discriminant analysis module 111 can identify a relevance of the disease to the medical care vector more accurately.

When determining that there is an adaptive relationship between the disease name i1 and the medical care event E, the discriminant analysis module 111 determines that the medical care event E is performed for the disease name i1. On the contrary, when determining that there is an adaptive relationship between the disease name i2 and the medical care event E, the discriminant analysis module 111 determines that the medical care event E is performed for the disease name i2 (804).

Further, in Step 804, the discriminant analysis module 111 assigns 1 to the combination of the disease name i and the medical care event E having an adaptive relationship, and assigns 0 to the combination of the disease name i and the medical care event E not having an adaptive relationship, to thereby generate a matrix (determinant analysis result matrix) indicating an adaptive relationship between the disease name i and the medical care event E. The discriminant analysis module 111 stores the determinant analysis result matrix into the memory 122 or the auxiliary storage device 123.

FIG. 12 is an explanatory diagram for illustrating a determinant analysis result matrix 1201 according to this embodiment.

The determinant analysis result matrix 1201 (result(i,E)) illustrated in FIG. 12 is an example of the matrix generated by the processing illustrated in FIG. 11. A column 1202 indicates the disease name i and a row 1203 indicates the medical care event E. When the medical care event E is performed for the disease name i, the component (i,E) is 1. Further, when the medical care event E is not performed for the disease name i, the component (i,E) is 0.

According to the discriminant analysis module 111 of this embodiment, a result of comparison between the feature vector that is generated based on the latest clinical information DB 101 and medical literature DB 102 and the discriminant model is used to generate a determinant analysis result matrix indicating an adaptive relationship between the disease name i and the medical care event E. With this, it is possible to acquire an adaptive relationship between the disease name i and the medical care event E based on the newly input information.

Further, the model construction module 110 and the discriminant analysis module 111 include values that are based on the frequency of complications, for example, the indicator change S, in the component of the feature vector, and thus the discriminant analysis module 111 of this embodiment can use natures of a disease, such as whether or not the disease is a complication or whether or not the disease is a chronic disease, as parameters for determining an adaptive relationship. With this, it is possible to accurately determine a relationship between the disease and the medical care event.

The model construction module 110 and the discriminant analysis module 111 may include the complication evaluation indicator T in the component of the feature vector instead of the indicator change S.

FIG. 13 is a flowchart for illustrating processing of the co-occurrence analysis module 112 of this embodiment.

The co-occurrence analysis module 112 acquires a medical literature file from the medical literature DB 102 (901).

Next, the co-occurrence analysis module 112 counts the number of medical literature files containing the disease name i and the medical care event E to generate a co-occurrence matrix containing the number of occurrences (i,E), which is a result of counting (902). Specifically, the co-occurrence analysis module 112 determines by full-text search whether or not terms of the disease name i1 and the medical care event E are contained in text indicating of medical literature files held by the medical literature DB 102.

FIG. 14 is an explanatory diagram for illustrating a co-occurrence matrix of this embodiment.

In the co-occurrence matrix illustrated in FIG. 14, a column 1001 indicates the disease name i and a row 1002 indicates the medical care event E. The cell corresponding to the disease name i and the medical care event E contains the number of co-occurrences F(i,E) calculated in Step 902.

After Step 902, the co-occurrence analysis module 112 calculates the co-occurrence frequency matrix co(i,E) using Expression (5) for each disease name i and for each medical care event E based on the generated co-occurrence matrix to generate a co-occurrence frequency matrix 1301 (903).

$$co(i,E)=F(i,E)/\Sigma F(i,E) \qquad (5)$$

FIG. 15 is an explanatory diagram for illustrating the co-occurrence frequency matrix 1301 of this embodiment.

The co-occurrence frequency matrix 1301 illustrated in FIG. 15 is an example of the co-occurrence frequency matrix co(i,E) calculated in Step 903. A column 1302 indicates the disease name i and a row 1303 indicates the medical care event E. After Step 903, the processing illustrated in FIG. 13 is finished, and then Step 133 illustrated in FIG. 3 is also finished. The co-occurrence analysis module 112 stores the generated co-occurrence frequency matrix co(i,E) into the memory 122 or the auxiliary storage device 123.

The co-occurrence analysis module 112 can use the matrix indicating a relevance of the disease name i to the medical care event E, which is based only on the clinical information DB 101, for generation of the disease name-medical care event relevance table by generating the co-occurrence frequency matrix co(i,E).

After the information gain calculation module 108, the discriminant analysis module 111, and the co-occurrence analysis module 112 generate the information gain matrix, the determinant analysis result matrix, and the co-occurrence frequency matrix (after Steps 131, 132, and 133), respectively, the result integration module 106 generates the disease name-medical care event relevance table (Relation (i,E)) using Expression (6) (Step 134 of FIG. 3).

$$Relation(i,E)=IG(i,E)+results(i,E)+co(i,E) \qquad (6)$$

FIG. 16 is an explanatory diagram for illustrating a disease name-medical care event relevance table 1401 of this embodiment.

The disease name-medical care event relevance table 1401 illustrated in FIG. 16 is an example of the disease name-medical care event relevance table (Relation(i,E)). A column 1402 indicates the disease name i and a row 1403 indicates the medical care event E.

After Step 134, the output module 107 outputs the Relation(i,E). Further, the output module 107 may output via the IO interface 124 a combination of the disease name i and the medical care event E for which its adaptive relationship satisfies a predetermined criterion based on the generated disease name-medical care event relevance table 1401. With this, the user can grasp medical knowledge indicating a predetermined relationship between the disease and the medical care event.

Figures 17, 18:
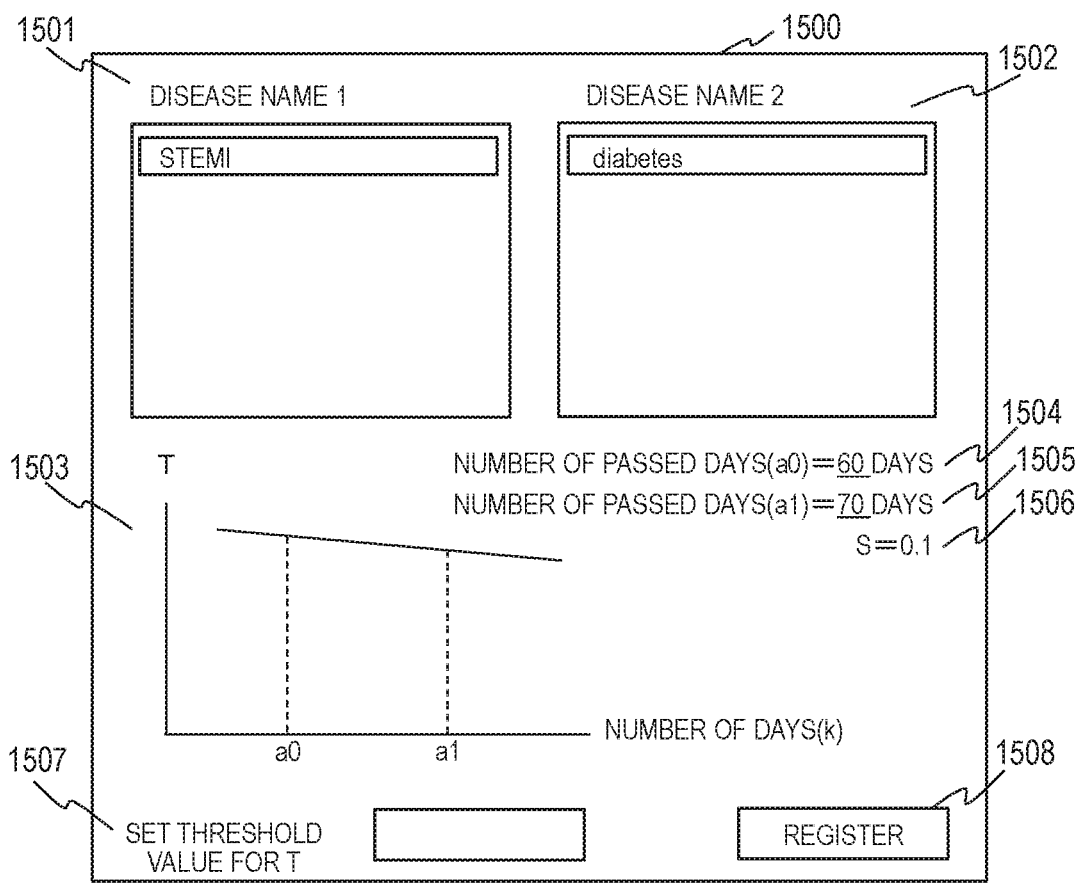
FIG. 17 is an explanatory diagram for illustrating a screen for displaying the disease name-medical care event relevance table of this embodiment.
FIG. 18 is an explanatory diagram for illustrating a screen for outputting the complication evaluation indicator T and the indicator change S of complications of this embodiment.

FIG. 17 is an explanatory diagram for illustrating a screen 1800 for displaying the disease name-medical care event relevance table of this embodiment.

The output module 107 may output, for example, data for displaying the screen 1800 via the IO interface 124. The screen 1800 includes an area 1801 and an area 1802.

The area 1801 is an area for allowing an operator to select content to be displayed on the screen 1800. The area 1801 illustrated in FIG. 17 includes display for selecting the information gain matrix, the co-occurrence frequency matrix, and the disease name-medical care event relevance table, but may include, for example, display for selecting the determinant analysis result matrix. Through display of a plurality of generated matrices, the operator can grasp relationships between disease names and medical care events, which are determined from different perspectives.

The area 1802 is an area for displaying content selected in the area 1801. When the disease name-medical care event relevance table is selected in the area 1801, the area 1802 displays content of the disease name-medical care event relevance table.

Further, the output module 107 may output via the IO interface 124 the complication evaluation indicator T and the indicator change S calculated in the discriminant analysis module 111.

FIG. 18 is an explanatory diagram for illustrating a screen 1500 for outputting the complication evaluation indicator T and the indicator change S of complications of this embodiment.

The output module 107 outputs, for example, data for displaying the screen 1500 via the IO interface 124. The screen 1500 is an example of the screen for visualizing a temporal change amount of the complication evaluation indicator T(i1,i2,k) relating to two disease names (disease name i1, disease name i2) and displaying the value of the indicator change S. The screen 1500 includes areas 1501 to 1508.

The area 1501 is a list box for selecting the disease name i1, and the area 1502 is a list box for selecting the disease name i2. The area 1503 displays a change in value of the complication evaluation indicator T(i,E,k) from the date t0 until the number of days k have passed with respect to the disease name i1 and the disease name i2 selected in the areas 1501 and 1502, respectively.

The area 1504 is an area for setting the number of days a0, and the area 1505 is an area for setting the number of days a1. The areas 1504 and 1505 are, for example, text boxes. The model construction module 110 calculates the indicator change S(i,E) by the processing of Step 703 with respect to the number of days a0 and the number of days a1 set in the areas 1504 and 1505, respectively. The area 1506 displays the calculated indicator change S(i,E).

The operator can grasp the values of the complication evaluation indicator T(i,E,k) and the indicator change S(i,E) for a combination of the disease name i1 and the disease name i2 and the number of days k by referring to the screen 1500. With this, it is possible to determine whether or not the disease name i1 and the disease name i2 are complications.

Further, the operator can determine a candidate of the predetermined threshold value T0 to be compared with the complication evaluation indicator T in Step 802 by referring to a change in the graph of the area 1503. When determining the candidate of the threshold value, the operator can input the candidate into the area 1507, and set the predetermined threshold value by clicking on a registration button of the area 1508.

For example, the operator can set the appropriate threshold value T0 by confirming in the area 1503 a change in the complication evaluation indicator T(i,E,k) when one of two disease names is a chronic disease and a change in the complication evaluation indicator T(i,E,k) when one of two disease names is an acute complication.

This invention is not limited to the above-described embodiments hut includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, and processors, for all or a part of them, may be implemented by hardware: for example, by designing an integrated circuit. The above-described configurations and functions may be implemented by software, which means that a processor interprets and executes programs providing the functions. The information of programs, tables, and files to implement the functions may be stored in a storage device such as a memory, a hard disk drive, or an SSD (Solid State Drive), or a storage medium such as an IC card, or an SD card.

Further, the processing illustrated in FIG. 6, FIG. 9, FIG. 10, FIG. 11, and FIG. 13 may be executed by function modules separated for each processing. For example, the discriminant analysis module 111 may be separated into a reading function module configured to execute Step 801, an indicator change calculation function module configured to execute Step 802, a syntax analysis function module configured to execute Step 803, and a matrix generation function module configured to execute Step 804.

The drawings shows control lines and information lines as considered necessary for explanations but do not show all control lines or information lines in the products. It can be considered that almost of all components are actually interconnected.

What is claimed is:

1. A computer system, comprising:
   a processor; and
   a memory,
   wherein the processor is configured to:
      acquire clinical information containing a plurality of cases, each of the plurality of cases indicating a disease of a patient and a medical care event performed on the patient;
      acquire literature information containing literature for indicating a name of the disease and a word indicating the medical care event;
      calculate a frequency of one case indicating a combination of a plurality of diseases based on the clinical information, to store the calculated frequency into the memory;
      analyze the literature information using each of the name of the disease and the word indicating the medical care event, to store an analysis result into the memory;
      acquire a criterion for determining a disease for which the medical care event has been performed;
      acquire first relevance information for indicating whether the medical care event has been performed for the disease based on the analysis result, the calculated frequency, and the acquired criterion, to store the first relevance information into the memory; and
      generate medical information for indicating a relationship between the medical care event and the disease based on the first relevance information;
   wherein the clinical information comprises a plurality of cases indicating medical care events that have been performed in a plurality of different periods elapsed since a predetermined start day,
   wherein the processor is configured to:
      calculate a plurality of the frequencies based on cases in the plurality of different periods elapsed;
      calculate a temporal change amount in frequency based on the plurality of the calculated frequencies;
      generate a feature vector containing a component for indicating the analysis result and a component for indicating the calculated temporal change amount; and
      acquire the first relevance information based on the generated feature vector and the acquired criterion.

2. The computer system according to claim 1, wherein the processor is configured to calculate the frequency by dividing a number of cases indicating both of a first disease and a second disease by a number of cases indicating at least the first disease.

3. The computer system according to claim 1, wherein the processor is configured to:
   calculate a first frequency of occurrence of a medical care event that has been performed within a period from the predetermined start day until a first day has passed, indicating a combination of the plurality of diseases;
   calculate a second frequency of occurrence of the medical care event that has been performed within a period from the predetermined start day until a second day later than the first day has passed, indicating the combination of the plurality of diseases; and calculate the temporal change amount based on a difference between the first frequency and the second frequency.

4. The computer system according to claim 1,
wherein literature contained in the literature information comprises a plurality of sentences, and
wherein the processor is configured to:
    identify a position of each of the name of the disease and the word indicating the medical care event in the plurality of sentences by analyzing the literature information; and
    generate as the analysis result information for indicating a relationship between each of the name of the disease and the word indicating the medical care event in the plurality of sentences based on the identified position.

5. The computer system according to claim 1, wherein the processor is configured to:
    select a disease and a medical care event from the clinical information;
    acquire second relevance information for indicating how frequently the selected medical care event is performed for the selected disease by identifying a number of cases contained in the clinical information, a number of cases indicating the selected disease, and a number of cases indicating the selected medical care event; and
    generate the medical information based on the first relevance information and the second relevance information.

6. The computer system according to claim 1, wherein the processor is configured to:
    acquire third relevance information for indicating a frequency of the name of the disease and the word indicating the medical care event co-occurring in the literature information; and
    generate the medical information based on the third relevance information and the first relevance information.

7. The computer system according to claim 6, wherein the processor is configured to:
    generate data for displaying the third relevance information and the generated medical information; and
    output the generated data.

8. The computer system according to claim 1, wherein the processor is configured to:
    acquire a medical dictionary containing words relating to medicine; and
    acquire from the medical dictionary a word other than the name of the disease as a word indicating the medical care event.

9. An information processing method, which is executed by a computer system comprising a processor and a memory, the information processing method comprising:
    acquiring, by the processor, clinical information containing a plurality of cases, each of the plurality of cases indicating a disease of a patient and a medical care event performed on the patient, and acquiring literature information containing literature for indicating a name of the disease and a word indicating the medical care event;
    calculating, by the processor, a frequency of one case indicating a combination of a plurality of diseases based on the clinical information, to store the calculated frequency into the memory;
    analyzing, by the processor, the literature information using each of the name of the disease and the word indicating the medical care event, to store an analysis result into the memory;
    acquiring, by the processor, a criterion for determining a disease for which the medical care event has been performed;
    acquiring, by the processor, first relevance information for indicating whether the medical care event has been performed for the disease based on the analysis result, the calculated frequency, and the acquired criterion, to store the first relevance information into the memory; and
    generating, by the processor, medical information for indicating a relationship between the medical care event and the disease based on the first relevance information;
    wherein the clinical information comprises a plurality of cases indicating medical care events that have been performed in a plurality of different periods elapsed since a predetermined start day,
    wherein the calculating a frequency comprises calculating, by the processor, a plurality of the frequencies based on cases in the plurality of different periods elapsed, and
    wherein the acquiring first relevance information comprises:
        calculating, by the processor, a temporal change amount in frequency based on the plurality of the calculated frequencies;
        generating, by the processor, a feature vector containing a component for indicating the analysis result and a component for indicating the calculated temporal change amount; and
        acquiring, by the processor, the first relevance information based on the generated feature vector and the acquired criterion.

10. The information processing method according to claim 9, wherein the calculating a frequency comprises calculating, by the processor, the frequency by dividing a number of cases indicating both of a first disease and a second disease by a number of cases indicating at least the first disease.

11. The information processing method according to claim 9,
    wherein the calculating a frequency comprises:
        calculating, by the processor, a first frequency of occurrence of a medical care event that has been performed within a period from the predetermined start day until a first day has passed, indicating a combination of the plurality of diseases;
        calculating, by the processor, a second frequency of occurrence of the medical care event that has been performed within a period from the predetermined start day until a second day later than the first day has passed, indicating the combination of the plurality of diseases; and
    wherein the acquiring first relevance information comprises calculating, by the processor, the temporal change amount based on a difference between the first frequency and the second frequency.

12. The information processing method according to claim 9,
    wherein literature contained in the literature information comprises a plurality of sentences, and
    wherein the analyzing the literature information comprises:

identifying, by the processor, a position of each of the name of the disease and the word indicating the medical care event in the plurality of sentences by analyzing the literature information; and generating, by the processor, as the analysis result information for indicating a relationship between each of the name of the disease and the word indicating the medical care event in the plurality of sentences based on the identified position.

13. The information processing method according to claim 9, further comprising:

selecting, by the processor, a disease and a medical care event from the clinical information; and acquiring, by the processor, second relevance information for indicating how frequently the selected medical care event is performed for the selected disease by identifying a number of cases contained in the clinical information, a number of cases indicating the selected disease, and a number of cases indicating the selected medical care event, wherein the generating medical information comprises generating, by the processor, the medical information based on the first relevance information and the second relevance information.

\* \* \* \* \*